US008961951B2

(12) United States Patent
Blissard et al.

(10) Patent No.: US 8,961,951 B2
(45) Date of Patent: Feb. 24, 2015

(54) BACULOVIRUSES WITH ENHANCED VIRION PRODUCTION AND A METHOD FOR THE PRODUCTION OF BACULOVIRUSES

(75) Inventors: Gary Blissard, Ithaca, NY (US); Jian Zhou, Piscataway, NJ (US)

(73) Assignee: Boyce Thompson Institute for Plant Research, Ithaca, NY (US)

( * ) Notice: Subject to any disclaimer, the term of this patent is extended or adjusted under 35 U.S.C. 154(b) by 386 days.

(21) Appl. No.: 12/667,956

(22) PCT Filed: Jul. 3, 2008

(86) PCT No.: PCT/US2008/069132
§ 371 (c)(1),
(2), (4) Date: Jan. 6, 2010

(87) PCT Pub. No.: WO2009/014878
PCT Pub. Date: Jan. 29, 2009

(65) Prior Publication Data
US 2010/0323398 A1 Dec. 23, 2010

Related U.S. Application Data

(60) Provisional application No. 60/948,214, filed on Jul. 6, 2007.

(51) Int. Cl.
| | | |
|---|---|---|
| A01N 63/00 | (2006.01) | |
| C12P 21/06 | (2006.01) | |
| C12N 15/00 | (2006.01) | |
| C12N 15/09 | (2006.01) | |
| C12N 7/00 | (2006.01) | |
| C07K 14/005 | (2006.01) | |
| C12N 15/86 | (2006.01) | |

(52) U.S. Cl.
CPC ............... *C12N 7/00* (2013.01); *C07K 14/005* (2013.01); *C12N 15/86* (2013.01); *C07K 2319/735* (2013.01); *C12N 2710/14121* (2013.01); *C12N 2710/14143* (2013.01); *C12N 2760/16122* (2013.01); *C12N 2760/20222* (2013.01)
USPC ... 424/93.2; 435/69.1; 435/235.1; 435/320.1; 435/440

(58) Field of Classification Search
CPC .. C07K 14/005; C07K 2319/735; C12N 7/00; C12N 15/86; C12N 2710/14121; C12N 2710/14143; C12N 2760/20222
USPC ........... 424/93.2; 435/69.1, 235.1, 320.1, 440
See application file for complete search history.

(56) References Cited

U.S. PATENT DOCUMENTS

| | | | |
|---|---|---|---|
| 5,512,421 A | 4/1996 | Burns et al. | |
| 6,410,316 B1 | 6/2002 | Sheridan et al. | |
| 6,497,873 B1 | 12/2002 | Whitt et al. | |
| 6,607,912 B2 | 8/2003 | Blissard et al. | |
| 6,858,205 B2 | 2/2005 | Blissard et al. | |
| 2002/0115188 A1 | 8/2002 | Blissard et al. | |
| 2003/0072773 A1* | 4/2003 | Wertz et al. | |
| 2005/0100890 A1 | 5/2005 | Davidson et al. | |

FOREIGN PATENT DOCUMENTS

WO 2005038035 A2 4/2005

OTHER PUBLICATIONS

Lung et al., 2002, Journal of Virology, vol. 76, No. 11, p. 5729-5736.*
Robison et al., 2000, Journal of Virology, vol. 74, No. 5, p. 2239-2246.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
International Search Report and Written Opinion for PCT/US2008/069132, mailed Apr. 15, 2009, 8 pages.
Ayres et al., "The complete DNA sequence of *Autographa californica* Nuclear Polyhedrosis Virus", Virology, Aug. 1994, vol. 202, pp. 586-605.
Barsoum et al., "Efficient transduction of mammalian cells by a recombinant baculovirus having the vesicular stomatitis virus G glycoprotein", Hum. Gene Ther., Nov. 1997, vol. 8, pp. 2011-2018.
Bideshi et al., "The Trichoplusia ni granulovirus helicase is unable to support replication of *Autographa californica* multicapsid nucleopolyhedrovirus in cells and larvae of T. ni", J. Gen. Virol., 2000, vol. 81, pp. 1593-1599.
Blissard et al., "Baculovirus GP64 envelope glycoprotein is sufficient to mediate pH dependent membrane fusion", J. Virol., Nov. 1992, vol. 66, No. 11, pp. 6829-6835.
Boublik et al., "Eukaryotic virus display: engineering the major surface glycoprotein of the *Autographa californica* nuclear polyhedrosis virus (AcNPV) for the presentation of foreign proteins on the virus surface", Nat. Biotechnol., 1995, vol. 13, pp. 1079-1084.
Boyce et al., "Baculovirus-mediated gene transfer into mammalian cells", Proc. Natl. Acad. Sci. USA, Mar. 1996, vol. 93, No. 6, pp. 2348-2352.
Ernst et al., "Baculovirus surface display: construction and screening of a eukaryotic epitope library", Nucleic Acids Res., 1998, vol. 26, pp. 1718-1723.
Friesen, P. D., and Miller, L. K. 2001. Insect Viruses, p. 599-628. In D. M. Knipe and P. M. Howley (ed.), Fields Virology, Fourth Edition, vol. 1. Lippincott Williams & Wilkins, Philadelphia.
Hefferon et al., "Host cell receptor binding by baculovirus GP64 and kinetics of virion entry", Virology, Jun. 1999, vol. 258, No. 2, pp. 455-468.

(Continued)

*Primary Examiner* — Shin Lin Chen
(74) *Attorney, Agent, or Firm* — Brown & Michaels, PC

(57) ABSTRACT

The present invention provides a method for restoring budding capability to GP64null baculoviruses including gp64null AcMNPV by expressing therein a portion of the VSV G protein gene or a truncated "stem" portion of the GP64 gene. Other embodiments provide methods to use portions of the G-stem or GP64 protein to target foreign proteins for display on virions.

5 Claims, 8 Drawing Sheets

(56) References Cited

OTHER PUBLICATIONS

Hofmann et al., "Efficient gene transfer into human hepatocytes by baculovirus vectors", Proc. Natl. Acad. Sci. USA, Oct. 1995, vol. 92, pp. 10099-10103.

Kaikkonen et al., "Truncated vesicular stomatitis virus G protein improves baculovirus transduction efficiency in vitro and in vivo", Gene Ther., Feb. 2006, vol. 13 No. 4, pp. 304-312.

Kitagawa et al., "Ligand-directed gene targeting to mammalian cells by pseudotype baculoviruses", J. Virol., Mar. 2005, vol. 79, No. 6, pp. 3639-3652.

Kost et al., "Baculovirus as versatile vectors for protein expression in insect and mammalian cells", Nat. Biotechnol., May 2005, vol. 23, pp. 567-575.

Lung et al., "Pseudotyping *Autographa californica* Multicapsid Nucleopolyhedrovirus (AcMNPV): F Proteins from Group II NPVs Are Functionally Analogous to AcMNPV GP64", J. Virol., Jun. 2002, vol. 76, No. 11, pp. 5729-5736.

Makela et al., "Enhanced baculovirus-mediated transduction of human cancer cells by tumor-homing peptides", J. Virol., Jul. 2006, vol. 80, pp. 6603-6611.

Mangor et al., "A GP64-Null Baculovirus Pseudotyped with Vesicular Stomatitis Virus G Protein", J. Virol., Mar. 2001, vol. 75, No. 6, pp. 2544-2556.

Monsma et al., "Identification of a membrane fusion domain and an oligomerization domain in the baculovirus GP64 Envelope Fusion Protein", J. Virol., Apr. 1995, vol. 69, No. 4, pp. 2583-2595.

Monsma et al., "The GP64 Envelope Fusion Protein is an essential baculovirus protein required for cell to cell transmission of infection", J. Virol., Jul. 1996, vol. 70, No. 7, pp. 4607-4616.

Mottershead et al., "Baculoviral display of the green fluorescent protein and rubella virus envelope proteins", Biochem. Biophys. Res. Commun., Sep. 1997, vol. 238, No. 3, pp. 717-722.

Neumann et al., "Plasmid-Driven Formation of Influenza Virus-Like Particles", J. Virol., Jan. 2000, vol. 74, No. 1, pp. 547-551.

Ojala et al., "Improved display of synthetic IgG-binding domains on the baculovirus surface", Technol. Cancer Res. Treat., Feb. 2004, vol. 3, No. 1, pp. 77-84.

Oker-Blom et al., Baculovirus display strategies: Emerging tools for eukaryotic libraries and gene delivery, Brief. Funct. Genomic. Proteomic., Oct. 2003, vol. 2, No. 3, p. 244-253.

Oomens et al., "Requirement for GP64 to drive efficient budding of *Autographa californica* Multicapsid Nucleopolyhedrovirus", Virology, Feb. 1999, vol. 254, No. 2, pp. 297-314.

Plonsky et al., "An analysis of the role of the target membrane on the gp64-induced fusion pore", Virology, Jan. 1999, vol. 253, No. 1, pp. 65-76.

Robison et al., "The Membrane-Proximal Stem Region of Vesicular Stomatitis Virus G Protein Confers Efficient Virus Assembly", J. Virol., Mar. 2000, vol. 74, No. 5, pp. 2239-2246.

Shoji et al., "Efficient gene transfer into various mammalian cells, including non-hepatic cells, by baculovirus vectors", J. Gen. Virol., Oct. 1997, Vol. 78, pp. 2657-2664.

Sinn et al., "Persistent gene expression in mouse nasal epithelia following feline immunodeficiency virus-based vector gene transfer", J. Virol., Oct. 2005, vol. 79, No. 20, pp. 12818-12827.

Tani et al., "In vitro and in vivo gene delivery by recombinant baculoviruses", J. Virol., Sep. 2003, vol. 77, No. 18, pp. 9799-9808.

Theilmann, D. A., et al. 2005. Baculoviridae, p. 177-185. In H. V. Van Regenmortel, D. H. L. Bishop, M. H. Van Regenmortel, and C. M. Fauquet (ed.), Virus Taxonomy: Eighth Report of the International Committee on Taxonomy of Viruses. Elsevier Academic Press, New York.

Yang et al., "Avian influenza virus hemagglutinin display on baculovirus envelope: cytoplasmic domain affects virus properties and vaccine potential", Mol. Ther., 2007, vol. 15, pp. 989-996.

Zhou et al., "Display of Heterologous Proteins on gp64null Baculovirus Virions and Enhanced Budding Mediated by a Vesicular Stomatitis Virus G-Stem Construct", J Virol., Feb. 2008, vol. 82, No. 3, pp. 1368-1377.

Zhou et al., "Identification of a GP64 Subdomain Involved in Receptor Binding by Budded Virions of the Baculovirus *Autographica californica* Multicapsid Nucleopolyhedrovirus", J. Virol., May 2008, vol. 82, No. 9, pp. 4449-4460.

Zhou et al. "Mapping the conformational epitope of a neutralizing antibody (AcV1) directed against the AcMNPV GP64 protein", Virology, Sep. 2006, vol. 352, No. 2, pp. 427-437.

Jayakar, H. R., E. Jeetendra, and M. A. Whitt. 2004. Rhabdovirus assembly and budding. Virus Research 106:117-132.

Kaikkonen Mu et al. "Truncated Vesicular Stomatitis Virus G Protein Improves Baculovirus Transduction Efficiency in Vitro and in Vivo." Gene Ther. Feb. 2006 ;vol. 13 No. 4 : p. 304-12.

Baekelandt V et al. "Characterization of Lentiviral Vector-Mediated Gene Transfer in Adult Mouse Brain." Hum Gene Ther. May 2002 vol. 13 No. 7: p. 841-53.

Jeetendra E et al. "The Membrane-Proximal Domain of Vesicular Stomatitis Virus G Protein Functions As a Membrane Fusion Potentiator and Can Induce Hemifusion." J Virol. Dec. 2002. vol. 76 No. 23: p. 12300-11.

\* cited by examiner

Figure 1 Construction of GP64 knockout viruses carrying the "stem" region of the VSV G protein, and G-Stem Fusions

A Knockout of gp64 in AcMNPV

AcMNPV bacmid (bMON14272)
v-cath  gp64  p24  gp16  pp34 v-cath  cat  p24  gp16  pp34
107325-108039    109761-112049

B Insertion of the VSV-G "Stem" construct in the polyhedrin locus of gp64null AcMNPV cMyc-G-Stem VSV G
421  463  482  511
N      TM    CTD   C
SP  cMyc
(GP64) epitope tag p6.9    64pro  EcoR I
GUS    cMyc-G-Stem
       Pst I            Xba I Gm^r
Tn7R    SV40    Tn7L
        Poly A cat gp64
locus   polyh locus
        AcMNPV bacmid
        (gp64null)

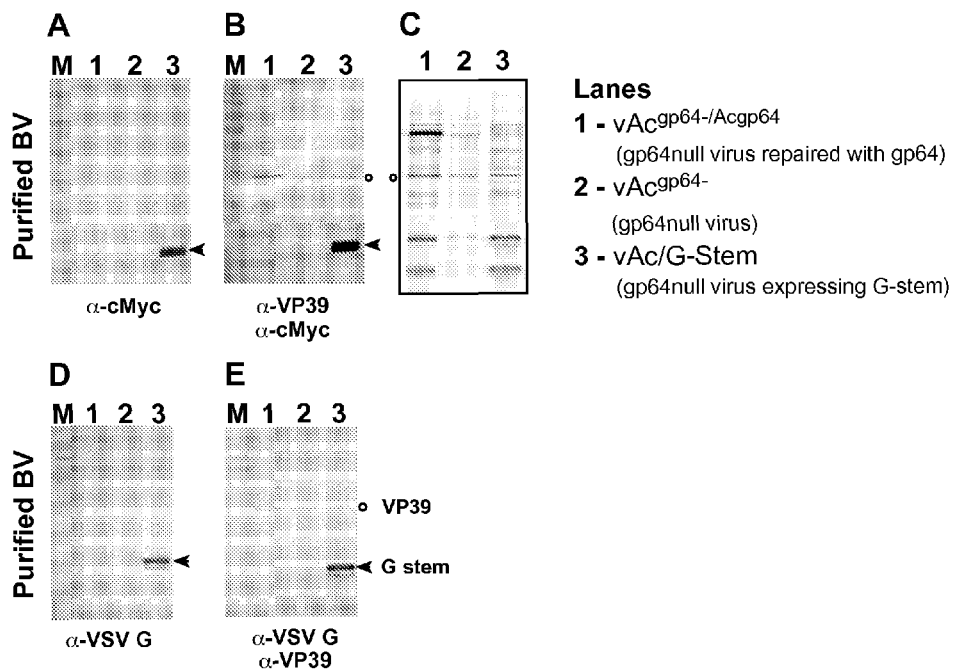
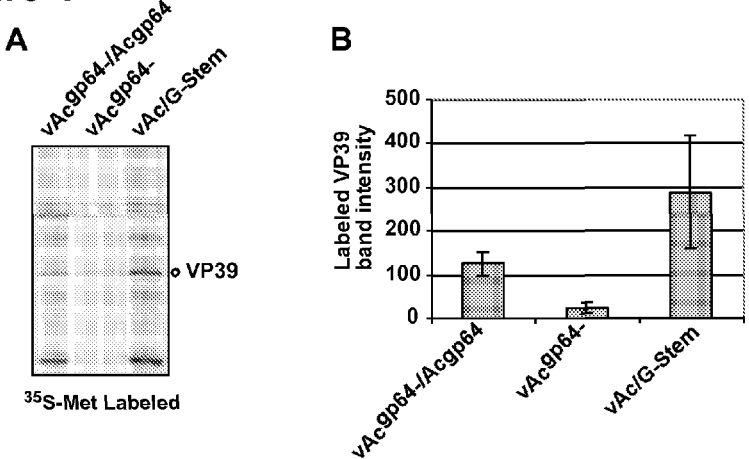

Figure 5
A G-Stem Fusions in gp64null AcMNPV
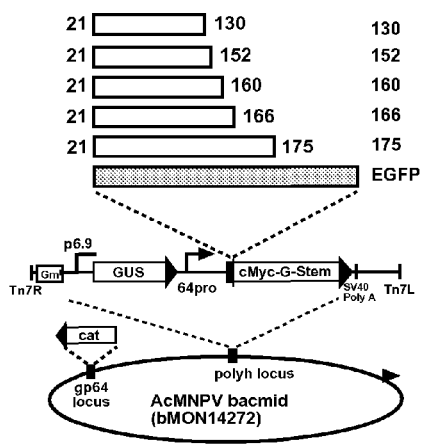
B G-Stem Fusions
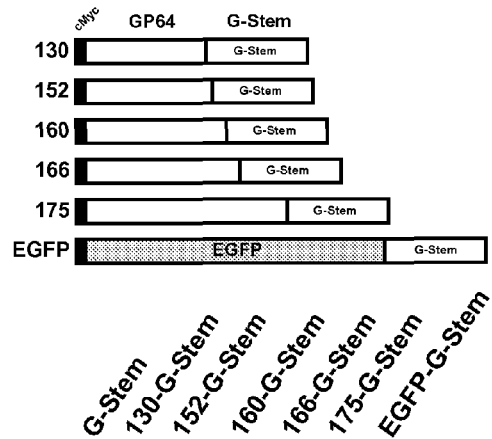
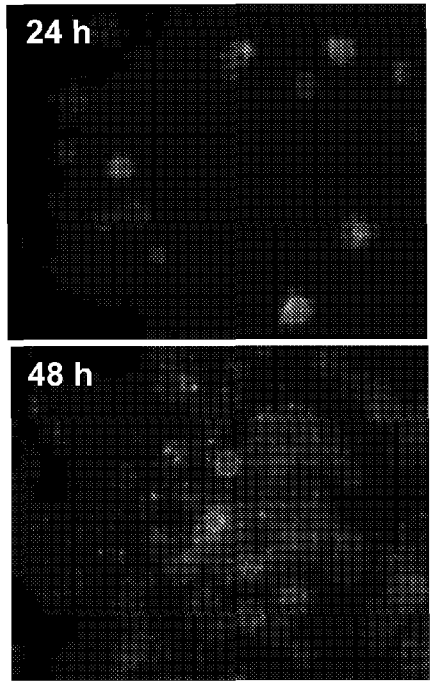
EGFP-G-Stem
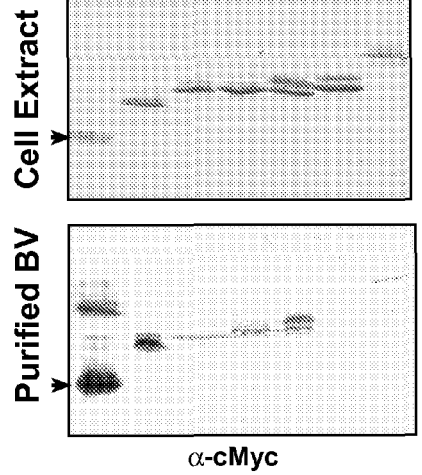
α-cMyc

Figure 6
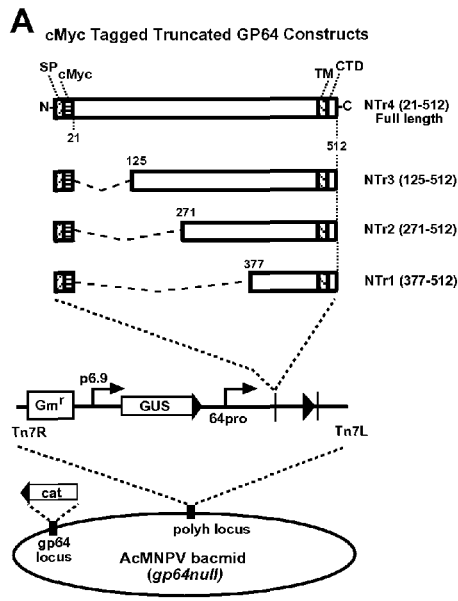
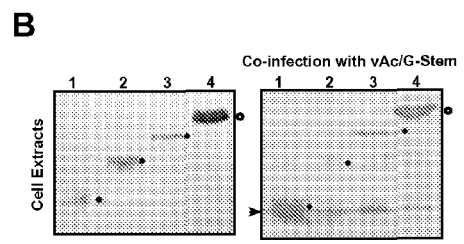
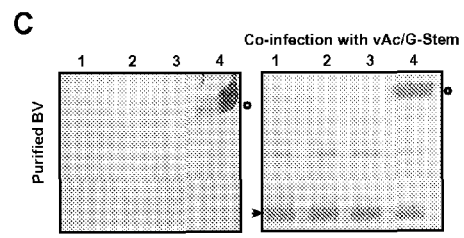
Lanes:
1: NTr1(377-512)
2: NTr2(271-512)
3: NTr3(125-512)
4: NTr4(21-512)
○ Full length GP64, NTr4 (21-512)
▶ G-stem Protein
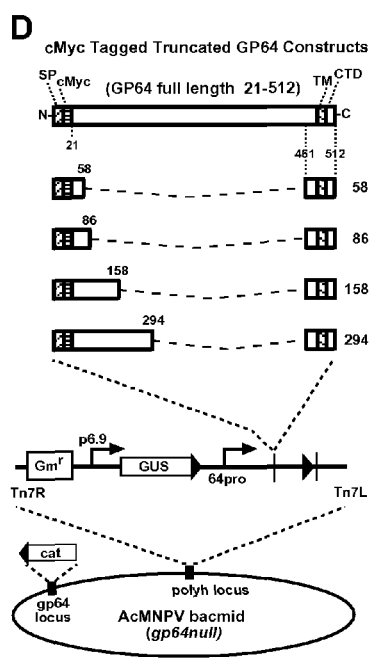
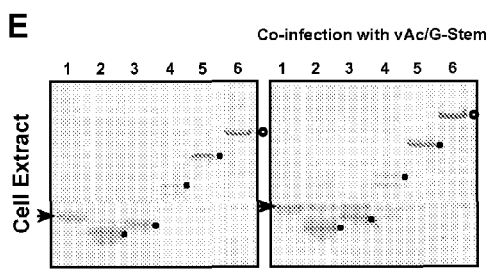
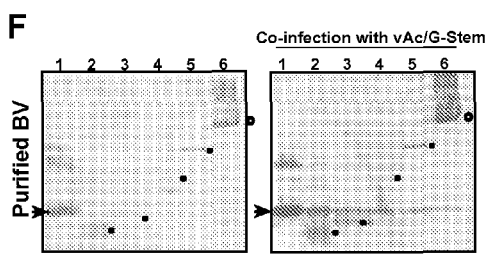
Lanes
1. vAc/G-Stem
2. vAc/58-TM-CTD
3. vAc/86-TM-CTD
4. vAc/158-TM-CTD
5. vAc/294-TM-CTD
6. vAc/cMyc-GP64 (full-length) ○
▶ G-stem Protein

G Rescue of BV Budding from gp64null AcMNPV with G-stem and Display of Heterologous Proteins on BV Virions are produced in Sf9-Op1D cells gp64null + GP64-stem or GP64-stem fusion → Sf9 cells → Virion Budding is partially restored → GP64-stem fusion gp64null + VSV G-stem → Sf9 cells → Virion Budding is robust → BV with VSV G stem / VSV G-Stem Co-infection gp64null + VSV G-stem
gp64null + GP64-stem fusion → Sf9 cells → Virion Budding and display are optimized → VSV G-Stem, GP64-stem fusion / GP64-stem fusions are displayed on BV envelope

Figure 7

Strategies for Heterologous Protein Display on gp64null virions in the Presence of G-Stem Baculovirus genomes with a deleted gp64 gene can be propagated as infectious viruses, using cell line Sf9-Op1D, which expresses the OpMNPV GP64 protein vAc⁶⁴⁻
gp64 knockout
→ Stable cell line expressing OpMNPV GP64 / Sf9-Op1D cells / Virus without gp64 gene can bud and propagate → OpMNPV GP64 / GP64null virus (vAc64⁻)

GP64null virions produced and titred in Sf9-Op1D cells

Insert gene encoding "Stem" region of VSV G protein → Sf9 cells / Virion Budding is restored → VSV G Stem / BV with VSV G stem Insert gene encoding Envelope or Membrane protein → Sf9 cells / Virion Buds Efficiently and carries New Membrane Protein → VSV G Stem + Heterologous Protein Insert genes encoding G-Stem and Chimeric G-Stem Fusion → Sf9 cells / Virion Buds Efficiently and carries New Membrane Protein → VSV G Stem + Heterologous Fusion Protein Insert genes encoding G-Stem and Chimeric GP64 Fusion → Sf9 cells / Virion Buds Efficiently and carries New Membrane Protein → VSV G Stem + Heterologous Fusion Protein

- AcMNPV GP64
- OpMNPV GP64
- G-stem from VSV G
- Heterologous Envelope Protein
- Chimeric Envelope Protein (G-Stem + Heterologous Protein)
- Chimeric Envelope Protein (GP64-stem + Heterologous Protein)

SEQUENCE LISTING

<160> NUMBER OF SEQ ID NOS: 17

<210> SEQ ID NO 1
<211> LENGTH: 43
<212> TYPE: DNA
<213> ORGANISM: Artificial Sequence
<220> FEATURE:
<223> OTHER INFORMATION: Primer

<400> SEQUENCE: 1
aaggtaccga cacaatatgt ataggctacc atgcgaacaa ctc      43

<210> SEQ ID NO 2
<211> LENGTH: 36
<212> TYPE: DNA
<213> ORGANISM: Artificial Sequence
<220> FEATURE:
<223> OTHER INFORMATION: Primer

<400> SEQUENCE: 2
aaggtaccct gatacacccc cattgattcc aatttc      36

```
<210> SEQ ID NO 3
<211> LENGTH: 40
<212> TYPE: DNA
<213> ORGANISM: Artificial Sequence
<220> FEATURE:
<223> OTHER INFORMATION: Primer

<400> SEQUENCE: 3
gacaagcttc atcagatgca tattctgcac tgcaaagacc                    40

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
aatgaattct tcgaacatcc tcacattcaa                               30

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
aatctagatt actttccaag tcggttcatc tctat                         35

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
aagaattcgc ggagcactgc aacgcg                                   26

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
aagaattcgc gaaaacagtc gtcgctgt                                 28

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
aagaattcgt gattgttatt ctgccgcttc ac                            32

<210> SEQ ID NO 9
<211> LENGTH: 27
<212> TYPE: DNA
<213> ORGANISM: Artificial Sequence
<220> FEATURE:
<223> OTHER INFORMATION: Primer
```

-continued

```
<400> SEQUENCE: 9
aagaattctt tgttgcacgt gtggtgc                                          27

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
aagaattcaa tgccgcatcg ccacga                                           26

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
aagaattcga gcctgctgta cattttcgaa gtg                                   33

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
aagaattcgt gagcaagggc gaggagctgt                                       30

<210> SEQ ID NO 13
<211> LENGTH: 37
<212> TYPE: DNA
<213> ORGANISM: Artificial Sequence
<220> FEATURE:
<223> OTHER INFORMATION: Primer

<400> SEQUENCE: 13
aagaattcct tgctagcctt gtacagctcg tccatgc                               37

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
gcggtacccg tctccacgat ggtgatttc                                        29

<210> SEQ ID NO 15
<211> LENGTH: 27
<212> TYPE: DNA
<213> ORGANISM: Artificial Sequence
<220> FEATURE:
<223> OTHER INFORMATION: Primer

<400> SEQUENCE: 15
gcggtaccgc gtgtgttggg atccagc                                          27

<210> SEQ ID NO 16
```

```
<211> LENGTH: 29
<212> TYPE: DNA
<213> ORGANISM: Artificial Sequence
<220> FEATURE:
<223> OTHER INFORMATION: Primer

<400> SEQUENCE: 16
gcggtaccta cctggcactc gtccgtgtc                                29

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
gcggtacctc cctctgtgta cttggc                                   26
```

BACULOVIRUSES WITH ENHANCED VIRION PRODUCTION AND A METHOD FOR THE PRODUCTION OF BACULOVIRUSES

REFERENCE TO RELATED APPLICATIONS

This application claims one or more inventions which were disclosed in Provisional Application No. 60/948,214, filed Jul. 6, 2007, entitled "BACULOVIRUSES WITH ENHANCED VIRION PRODUCTION AND A METHOD FOR THE PRODUCTION OF BACULOVIRUSES". The benefit under 35 USC §119(e) of the United States provisional application is hereby claimed, and the aforementioned application is hereby incorporated herein by reference.

ACKNOWLEDGMENT OF GOVERNMENT SUPPORT

This invention was made with Government support under Grant No. R01-AI33657, awarded by the National Institutes of Health. The US Government has certain rights in the invention.

BACKGROUND OF THE INVENTION

1. Field of the Invention

The invention pertains to the field of virion production. More specifically, the invention pertains to methods for enhancing virion production in baculovirus strains, particularly GP64null baculoviruses, and a means to optionally express and display heterologous proteins on virus particles or virions.

2. Description of Related Art

Baculoviruses are large double stranded DNA viruses that have been studied as agents for biological control of insect pests, as expression vectors for high level production of heterologous proteins, and as transduction vectors and potential agents for human gene therapy. The latter applications derive from the observation that baculovirus virions can efficiently enter a variety of human and other animal cell types and deliver the baculovirus DNA genome to the nucleus of the cell. Viral entry is relatively efficient and promiscuous, permitting entry into many different cell types that are not permissive for viral replication. Expression of foreign proteins in heterologous (non-permissive) cells is achieved by engineering the coding sequence of a foreign gene under a promoter that is active in the target cell type. For example, protein expression in human cells is achieved by placing the coding region of the foreign gene under the control of a promoter that is active in human cells, e.g. a human cytomegalovirus (HCMV) early promoter. Attempts to expand the range of cells that are promiscuously entered by baculovirus *Autographa californica* multicapsid nucleopolyhedrovirus (AcMNPV) virions include studies in which the human Vesicular Stomatitis Virus envelope glycoprotein known as G (VSV G) was expressed in addition to the baculovirus envelope protein GP64. For many applications in gene therapy however, targeted entry of the baculovirus virion into specific cell types would be highly desirable in order to either positively modify or negatively affect the growth and/or survival of the target cell type. For example, cells infected with viruses such as HIV might be targeted for destruction or death. Alternatively, genetic defects might be corrected by expression of a protein in specific cell types. Thus, the ability to target baculovirus virion entry to specific cell types would be of great value as a biotechnological tool in medicine or gene therapy. However, because of the promiscuity of AcMNPV entry into heterologous cells, targeted entry is not currently possible with native virions.

AcMNPV is the baculovirus studied most extensively for gene therapy applications. AcMNPV requires the major envelope glycoprotein known as GP64 for virion production and viral entry. In the absence of GP64, baculovirus virion production is severely reduced and the virions that are produced are not infectious. Thus, GP64 is critical for the efficient production of virions and for the ability of those virions to enter host cells. Similarly, other baculoviruses such as LdMNPV, SeMNPV, or HaNPV require the so-called F envelope protein for entry. Studies have shown that virions of the baculovirus AcMNPV can be pseudotyped—that is, the GP64 protein can be replaced with the envelope protein from another virus. AcMNPV viruses lacking GP64 (gp64null) that express the human Vesicular Stomatitis Virus G (VSV G) protein are able to produce infectious virions. However, like GP64, entry mediated by the VSV G protein is known to be highly promiscuous. Thus, VSV G does not provide specificity in cell targeting. Studies pseudotyping AcMNPV with F envelope proteins from other baculoviruses showed that some but not all baculovirus F proteins could substitute for GP64. In addition, studies of baculovirus F proteins in pseudotyped retroviruses indicate that they may not be useful in gene therapy applications as they did not mediate efficient entry into mammalian (mouse) cells.

The failure of gp64null baculoviruses to efficiently produce infectious virus particles is a critical and unresolved issue that must be addressed in order to effectively use virions of baculoviruses like AcMNPV in gene therapy applications where cell type targeting is necessary or desirable. In addition to gene therapy applications, it may be desirable to display foreign proteins on the surface of a gp64null virion for other purposes, such as production of a therapeutic or a vaccine. With existing methodology, it is difficult to produce usable quantities of gp64null baculovirus particles containing heterologous envelope proteins. This problem presents a substantial constraint on the potential use of pseudotyped gp64null viruses. The present invention is directed to solving this problem and other problems that are associated with the production of virions or pseudotyped virions.

SUMMARY OF THE INVENTION

The present invention addresses the issue of inefficient budding from gp64null viruses. The following strategy was used: A membrane proximal fragment of the VSV G protein (hereinafter referred to as a G-stem) was cloned into the genome of a gp64null baculovirus. In a preferred embodiment of the invention, the G-stem polypeptide includes amino acid sequences from each of: the C-terminal portion of the ectodomain; the predicted transmembrane domain; and the predicted cytoplasmic domain. In a more preferred embodiment of the invention, the G-stem polypeptide includes a sequence of 20-130 amino acids from the C-terminal portion of the ectodomain; substantially all of the predicted transmembrane domain; and a sequence of from about 10 to substantially all of the amino acids that make up the predicted cytoplasmic tail domain. In another preferred embodiment of the invention, the VSV G stem polypeptide includes: about 42 amino acids from the C-terminal portion of the ectodomain; about 28 amino acids from the predicted transmembrane domain; and about 21 amino acids from the predicted cytoplasmic tail domain.

In addition to overcoming the budding defects, the methods of the present invention provide a means for displaying foreign proteins on the surface of gp64null baculovirus virions. Chimeric fusion proteins containing a G-stem polypeptide or a portion of GP64 can be targeted to gp64null virions produced by G-stem stimulated budding. In a preferred embodiment of the invention, these chimeric proteins contain a heterologous protein or protein fragment that confers cell-specific targeting and entry.

Virions which express heterologous proteins as produced by the methods of this invention can be used for a variety of purposes including:
1. Gene therapy targeted to one or many cell types.
2. Vaccine production where the display of a heterologous protein on the surface of a baculovirus particle elicits a more robust immune response.
3. Other applications involving display of a membrane or other protein on virus particles.

BRIEF DESCRIPTION OF THE DRAWINGS

FIG. 1A shows a strategy for generation of a gp64-null AcMNPV bacmid by homologous recombination in E. coli.

FIG. 1B shows a strategy for insertion of a VSV G-stem construct into the polyhedrin locus of the gp64null AcMNPV bacmid.

FIG. 3A shows a Western blot of purified virions challenged with an anti-cMyc antibody, and demonstrating rescue of virion production by G-stem expression.

FIG. 3B shows a Western blot of purified virions as in FIG. 3A challenged with an anti-cMyc antibody and an anti-VP39 antibody.

FIG. 3C shows the blot from FIGS. 3A and 3B (which contains $^{35}$S-met labeled purified virions) imaged on a PhosphorImager™ screen.

FIG. 3D shows a Western blot of purified virions challenged with an anti-VSV-G antibody.

FIG. 3E shows a Western blot of purified virions challenged with an anti-VSV-G antibody and an anti-VP39 antibody.

FIG. 4A shows a quantitative comparison of progeny budded virion (BV) production from Sf9 cells infected with several baculovirus constructs (vAc$^{gp64-/Acgp64}$, vAc$^{gp64-}$ and vAc/G-Stem).

FIG. 4B shows quantitative comparisons of the VP39 protein band as an indicator of budded virus production from various preparations as shown in FIG. 4A.

FIG. 5A shows a strategy for insertion of VSV G-Stem fusion protein gene constructs into the polyhedrin locus of a gp64null AcMNPV bacmid.

FIG. 5B shows representative G-stem fusion constructs and Western blot analyses of products from gp64null baculoviruses expressing each.

FIG. 5C shows fluorescence micrographs of cells infected with an EGFP-G-stem construct.

FIG. 6A shows a strategy for constructing a series of cMyc tagged GP64 constructs that are truncated at the N-terminus of the GP64 ectodomain.

FIG. 6B shows Western blot analysis of cell extracts from cells infected with gp64null viruses expressing the GP64 constructs shown in FIG. 6A (left panel) or co-infected with the viruses expressing the constructs from FIG. 6A and a virus expressing the VSV G-stem construct (right panel).

FIG. 6C shows Western blot analysis of purified budded virions from cells infected with viruses expressing the GP64 constructs shown in FIG. 6A (left panel) or co-infected with the viruses expressing the constructs from FIG. 6A and a virus expressing the VSV G-stem construct (right panel).

FIG. 6D shows the strategy for constructing a series of cMyc tagged truncated GP64 constructs. A series of constructs containing the GP64 "stem" domain and various portions of the GP64 ectodomain were generated.

FIG. 6E shows Western blot analysis of cell extracts from cells infected with viruses expressing the G-stem construct or the GP64-stem fusions alone (left panel) or co-infections of viruses expressing the GP64-stem fusions and a virus expressing the VSV G-stem construct (right panel).

FIG. 6F shows Western blot analysis of purified budded virions (BV) from cells infected with viruses expressing GP64-stem fusions (left panel) or co-infected with viruses expressing the GP64-stem fusions and a virus expressing the VSV G-stem construct (right panel).

FIG. 6G shows a diagrammatic representation of strategies used for infection or co-infection of Sf9 cells with viruses expressing fusion proteins containing the GP64-stem and display of the GP64-stem fusions on BV.

FIG. 7 shows strategies for display of heterologous proteins on the surface of gp64null AcMNPV budded virions.

DETAILED DESCRIPTION OF THE INVENTION

Figure 2:
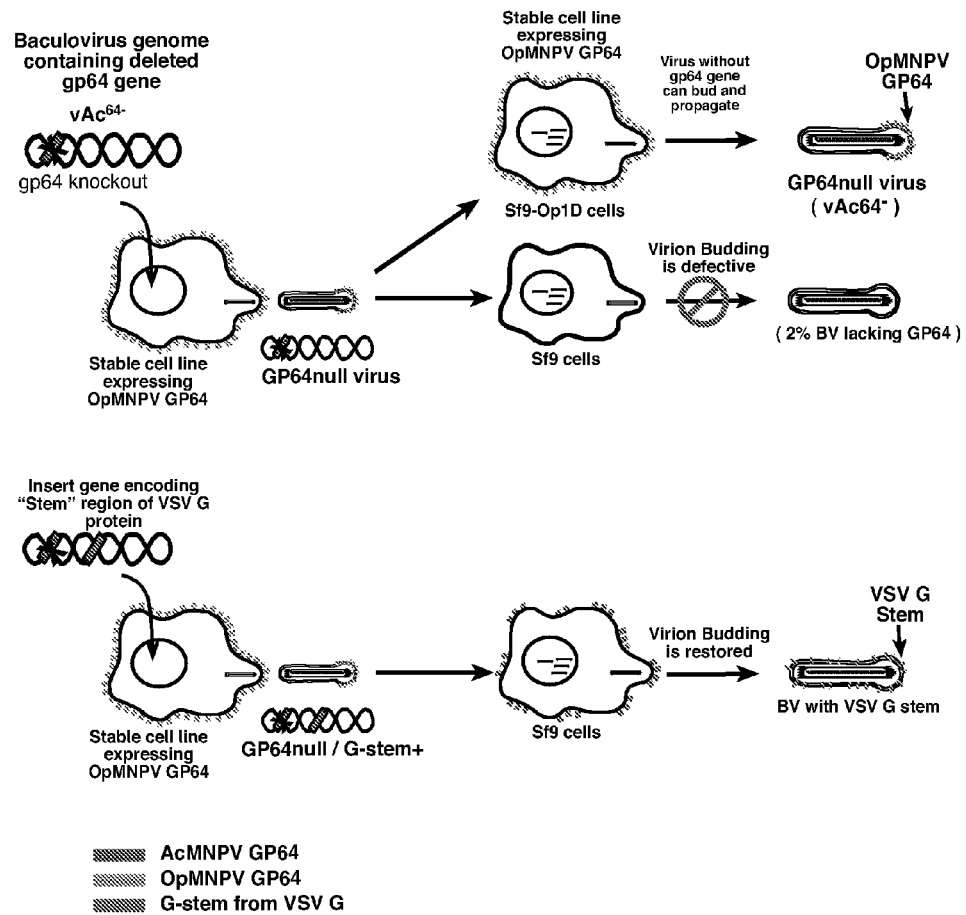
FIG. 2 shows a strategy for rescuing virion production by gp64null baculovirus infected cells under several conditions.

As noted above, baculoviruses such as AcMNPV containing a knockout in the gp64 gene are unable to produce virions efficiently in the absence of the GP64 protein and this represents a major obstacle to the use of gp64null viruses in research and biotechnology. The present invention provides a method to solve this and related problems.

The present invention provides methods for restoring efficient budding capability to GP64null baculoviruses including gp64null AcMNPV by expressing therein or otherwise providing a portion of the VSV G protein or a portion of GP64. Other embodiments provide methods to express foreign proteins on virions. By choosing stem constructs of the invention and including appropriate heterologous proteins that confer cell-specific targeting and entry, the invention provides a means for production of gp64null baculovirus virions capable of cell-specific entry. The use of G-stem or GP64-stem constructs as identified here, as chimeric fusions with heterologous proteins also provides a means of targeting proteins to the virion membrane or envelope. In addition, the methods of the present invention provide a means for vaccine production wherein the expression of a heterologous protein on the surface of a baculovirus particle elicits a more robust immune response. Finally, the invention enables other diverse applications as are well known to those skilled in the art where expression of a membrane or other protein on viral particles is desirable.

Although the VSV G protein and the GP64 proteins are discussed herein, stem constructs derived from envelope glycoproteins of other baculoviruses or other members of the Rhabdovirus family of negative-sense RNA viruses are also within the spirit of the present invention.

It was not obvious that VSV G-stem polypeptides would provide a solution to problems encountered with gp64null baculovirus budding. Indeed, several factors suggested that a VSV G-stem would not be compatible with baculoviruses. These factors include: baculoviruses (large DNA viruses with genomes of 100+ genes that replicate in the nucleus) are completely unrelated to rhabdoviruses like VSV (negative stranded RNA viruses with small genomes of only 5 open reading frames (ORFs) that replicate in the cytoplasm). In addition, VSV proteins bear no obvious amino acid sequence similarity to those of Baculoviruses and the virion structure of the two viruses appears to have little in common beyond superficial features of enveloped viruses. Despite these considerations, expression of G-stem constructs during infection by a gp64null baculovirus according to the methods of the present invention resulted in the efficient production of virions and thus rescued the severe budding defect observed in the gp64null virus.

In one embodiment of the invention, a truncated VSV G gene construct (referred to generically herein as G-stem constructs) was created and the gene was inserted into the AcMNPV baculovirus genome under the control of the baculovirus AcMNPV gp64 promoter. In a preferred embodiment of the invention, such VSV G gene constructs included an AcMNPV gene promoter and signal peptide, an epitope tag, and an N-terminally truncated VSV G gene fragment. An exemplary VSV G gene construct of the invention includes the AcMNPV gp64 promoter and signal peptide, a cMyc epitope tag (at the N-terminus of the mature protein), 42 amino acids from the VSV G ectodomain (positions 421 to 463), plus the predicted transmembrane (TM) and the cytoplasmic tail (CTD) domains of VSV G.

This G-stem construct was inserted into an AcMNPV bacmid containing a gp64 deletion, using a method described in Lung et al., 2002, J. Virol. 76, pages 5729-5736, herein incorporated by reference. Construction of the baculovirus bacmid is summarized in FIGS. 1A and 1B. FIG. 1A shows a strategy for generation of a gp64-null AcMNPV bacmid by homologous recombination in *E. coli*. The gp64 locus of the AcMNPV bacmid (bMON14272) is shown above a fragment that was used as a transfer vector to replace the gp64 locus with a chloramphenicol resistance gene (cat). Sequences included for homologous recombination (107325 to 108039 and 109761 to 112049) are indicated.

FIG. 1B shows a strategy for insertion of a VSV G-stem construct into the polyhedrin locus of the gp64null AcMNPV bacmid. The cassette inserted into the gp64null bacmid includes a p6.9 promoter-GUS reporter plus sequences encoding a truncated VSV G protein (VSV G-stem) under the control of a gp64 promoter (64pro). The VSV G-Stem construct encodes the gp64 signal peptide, followed by a cMyc tag and a truncated version of the VSV G protein that encodes 42 amino acids of the C-terminal portion of the VSV G ectodomain, plus the transmembrane (TM) and cytoplasmic tail domains (CTD) of VSV G. Numbers above the cMyc-G-Stem cassette (421-511) indicate amino acid sequence numbers from the VSV G protein. G-Stem fusion protein gene cassettes were inserted into the polyhedrin locus of a gp64null AcMNPV bacmid by Tn7-based transposition.

The resulting bacmid was used to generate a virus, designated vAc/G-Stem, by transfecting the bacmid into a stable cell line that constitutively expresses a wild type GP64 protein. One such cell line suitable for the invention is known as Sf9$^{Op1D}$. The strategy for propagation of the virus is summarized in FIG. 2.

FIG. 2 shows a strategy for rescuing virion production by gp64null baculovirus infected cells under several conditions. The diagram shows strategies for producing budded virions from gp64null viruses, using either a cell line (Sf9$^{Op1D}$) or a VSV G-stem construct. More specifically, a baculovirus genome contains a deleted gp64 gene (gp64 knockout, vAc$^{64-}$), and that baculovirus can be propagated in a stable cell line expressing OpMNPV GP64. When the GP64 null virus infects Sf9-Op1D, the cell line expressing OpMNPV GP64, the virus without the gp64 gene can bud and propagate, thus resulting in budding of a GP64null virus with OpMNPV GP64. When the GP64 null virus infects SF9 cells, the virus can enter the cells and partially replicate, but virion budding is defective, and results in only about 2-5% budded virions lacking GP64.

Alternatively, a gene encoding the "stem" region of the VSV G protein is inserted into the viral genome containing the gp64 knockout (vAc/G-Stem), and then propagated in the cell line expressing OpMNPV GP64. When the GP64null/G-stem+ virus is then used to infect Sf9 cells, virion budding is restored, resulting in budded virions displaying the VSV G stem.

To determine if a G-Stem had an effect on virion budding, an AcMNPV budding assay was performed. Sf9 cells were infected with control or G-Stem expressing gp64null viruses (previously generated and titred in Sf9$^{Op1D}$ cells). Next, progeny virions were metabolically labeled with $^{35}$S-methionine. Supernatants containing labeled progeny virions were collected and virions were purified by pelleting through 25% sucrose. In this budding assay, budded virions are isolated from the supernatant and only progeny virions are labeled. Progeny virions were isolated in this manner from Sf9 cells infected with viruses vAc$^{gp64-}$ (a gp64null virus), vAc$^{gp64-/Acgp64}$ (a gp64null virus that was repaired by reinserting a gp64 gene), and vAc/G-Stem (a gp64null virus that expressed a G-Stem construct).

FIGS. 3A-3E shows Western blot analyses of purified virions produced by gp64null baculovirus under several conditions. The Western blot analyses using both anti-cMyc and anti-VSV G antibodies show G-Stem protein in purified budded virions from the cells infected with the vAc/G-stem virus.

The Western blot was challenged with an anti-cMyc antibody and analyzed (FIG. 3A), then the same blot was challenged with an anti-VP39 antibody and analyzed again (FIG. 3B). In addition, the same blot was imaged on a PhosphorImager™ screen (FIG. 3C) to detect labeled virion proteins. Because VP39 (the major capsid protein) is highly abundant in virions and the quantity of VP39 per virion appears to be constant, the VP39 protein in virion preparations is typically used as an indicator of relative virion quantity. FIG. 3D shows a Western blot challenged with anti-VSV G and FIG. 3E shows a Western blot challenged with anti-VSV G and anti-VP39. Lane 1 of FIGS. 3A-3E and FIGS. 4A-4B shows budded virions purified from Sf9 cells infected with vAc$^{gp64-/Acgp64}$. Lane 2 shows budded virions purified from Sf9 cells infected with vAc$^{gp64-}$ and lane 3 shows budded virions purified from Sf9 cells infected with vAc/G-Stem. The open circles in these figures indicate the position of the major capsid protein, VP39, of AcMNPV and arrowheads indicate the positions of the cMyc-tagged G-stem protein, as detected by the respective antibodies. Purified virions were examined by SDS-PAGE and Western blotting.

FIG. 4A shows a quantitative comparison of budded virion (BV) production from Sf9 cells infected with several baculoviruses: vAc$^{gp64-/Acgp64}$, vAc$^{gp64-}$ and vAc/G-Stem. More specifically, FIG. 4A shows a PhosphorImager™ analysis of purified labeled virions. Sf9 cells were infected with each virus, labeled with $^{35}$S-Methionine, and progeny virions were isolated from infected cell supernatants by centrifugation of the supernatant through a sucrose cushion, followed by separation of virions on equilibrium sucrose density gradients. Virions derived from equivalent amounts of infected cell culture supernatants were loaded onto SDS-PAGE gels and examined by phosphorImager™ analysis of labeled virion proteins.

Quantitative comparisons of $^{35}$S-Methionine labeled VP39 bands from budded virion preparations derived from equivalent quantities of cell supernatants indicated that virion production in the gp64null virus expressing a G-stem construct (virus vAc/G-Stem) was approximately 2.27 times higher than that of the virus expressing wild type GP64, and about 11 times higher than that detected from the gp64null virus (FIGS. 4A-4B). FIG. 4A is one representative example from among 3 sets of independently labeled budded virion profiles and the graph in FIG. 4B was generated with data from three independently labeled viral profiles. FIG. 4B shows quantitative comparisons of the VP39 protein band from various preparations as shown in FIG. 4A. Quantification data represent averages and standard deviations derived from three independently labeled BV preparations.

These data show that expression of a VSV G-Stem construct in the context of a gp64null baculovirus resulted in the rescue of the severe budding defect caused by the absence of the GP64 protein. Indeed, preliminary measurements suggest that budding stimulated by a G-stem construct may even exceed that from a virus expressing the wild-type GP64 protein. Thus, using the methods of the present invention, budded virions that contain no native GP64 protein can be efficiently generated. It is further possible to produce virions that express foreign proteins in the absence of a native GP64 protein using these methods. Such virions have important applications in biotechnology, including applications in vaccine development and gene therapy.

In another embodiment, expression of the G-stem construct under a stronger promoter such as the AcMNPV polyhedrin or p10 promoter may result in even higher levels of GP64null virion production.

A similar system is applicable to related baculoviruses that carry an F protein and no GP64 protein, in the following manner. The F gene is deleted from the genome of a virus such as a group II NPV or GV, by methods similar to those used for deleting the gp64 gene from AcMNPV, using a cell line engineered to express the F protein or a suitable homolog. Budding by the resulting F-null virus is then rescued by providing either a G-stem construct, a GP64-stem construct, or a similar portion of the F protein. Additionally, heterologous peptides or proteins may be displayed by generating fusions with the stem region of the homologous F protein. Alternatively, heterologous proteins (GP64, VSV G, etc.) could be used as a source for the stem regions that are used for generating fusions and targeting the proteins to the virion.

Several embodiments using methods of the present invention to express foreign proteins on the surface of gp64null AcMNPV virions are disclosed herein. A first embodiment includes expression of one or more native membrane or envelope proteins in combination with a G-stem construct in gp64null virus infected cells. A second embodiment of the invention includes expression of protein fusions containing all or a portion of the ectodomain of a foreign protein fused to a G-stem construct. A third embodiment of the invention includes the expression of protein fusions containing all or a portion of the ectodomain of a foreign protein fused to a portion of the GP64 protein including the transmembrane and cytoplasmic domains of GP64. A fourth embodiment uses one or more portions of other baculovirus virion membrane proteins (for instance Ac23 or F proteins from other baculoviruses) as the "stem" region for fusions with one or more foreign proteins. In the second and third embodiments above, a G-stem construct alone could be expressed separately to provide the budding function. Alternatively in other preferred embodiments, foreign proteins fused to a G-stem provide sufficient rescue of budding in the absence of a separately expressed G-stem construct.

As examples of the embodiments described above, a series of G-stem fusion constructs was generated. A G-stem as described previously was fused to the C-terminus of either the enhanced green fluorescent protein (EGFP) or various portions of the GP64 ectodomain. These G-stem fusion constructs were then inserted into a gp64null baculovirus. The strategy for generating these constructs is outlined in FIG. 5A. FIG. 5A shows a strategy for insertion of VSV G-Stem fusion protein gene constructs into the polyhedrin locus of a gp64null AcMNPV bacmid. Constructs were generated to express peptides or proteins fused with a VSV G-Stem and under the control of the gp64 promoter (64pro). Peptides fused to the G-stem included the EGFP protein as well as portions of the AcMNPV GP64 protein. Peptides derived from the GP64 protein (designated 130, 152, 160, 166, and 175) were fused to the G-Stem fusion protein. The cassette inserted into the bacmid also included a p6.9 promoter-GUS reporter construct.

Expression and analysis of G-Stem fusion proteins by Western blot analysis and immunofluorescence microscopy are illustrated in FIGS. 5B-5C. FIG. 5B shows representative G-stem fusion constructs and Western blot analyses of products from gp64null baculoviruses expressing each. Cell extracts or purified BV preparations derived from Sf9 cells infected with the gp64null viruses expressing G-stem fusion constructs were examined for protein expression using Western blot analysis with an anti-cMyc antibody. All G-stem constructs contained a cMyc epitope tag. Analysis of cell extracts shows that each G-stem construct was stably expressed in the infected cells, and analysis of purified BV shows that various G-stem constructs were targeted to and assembled into the BV. FIG. 5C shows fluorescence micrographs of cells infected with an EGFP-G-stem construct. Micrographs show fluorescence from infected cells at 24 and 48 hours post infection.

In a preferred embodiment of the invention, G-stem polypeptides were fused to peptides of about 130 to 175 amino acids in length (derived from the GP64 ectodomain), or fused to EGFP, then cloned under the GP64 promoter and inserted into a gp64null AcMNPV virus genome. The resulting viruses were propagated in appropriate host cells such as Sf9$^{Op1D}$ cells then used to infect Sf9 cells. Expression of the fusion proteins was detected by Western blot analysis of cell extracts or purified BV using an anti-cMyc antibody. All fusion constructs were expressed well in infected Sf9 cells (FIG. 5B, upper panel, lanes 2-7). Examination of cells infected with the virus containing the EGFP-G-stem fusion by immunofluorescence microscopy (FIG. 5C) further demonstrated expression of that construct in the infected cells. All G-stem fusions tested, except a fusion containing a 175 amino acid region from GP64, were detected in purified preparations of BV (FIG. 5B, lower panel). The G-stem construct alone (unfused) mediated robust budding (FIGS. 3A-3E and 4A-4B) and was found in abundance in the BV and at higher levels than that observed with the fusion constructs (FIG. 5B, lower panel; compare lane 1 to 2-7, arrow). Using the single cMyc epitope present on each construct, these data show clear relative differences in detection of the different G-stem fusion constructs and confirm that most (all but one) of these fusion constructs were a) capable of mediating virion budding, and b) targeted to, and displayed on gp64null virions. Thus, because most of the G-stem fusion protein constructs evaluated were found in the purified virion preparations, these data show that this is a viable strategy for generating BV and displaying foreign proteins on AcMNPV gp64null virions.

In an example of those embodiments of the invention that include the expression of protein fusions containing all or a portion of the transmembrane and cytoplasmic domains of the GP64 protein, a series of baculoviruses that expressed proteins containing a GP64 "stem" domain and various portions of the GP64 ectodomain was generated. FIG. 6 shows an overall strategy for mapping GP64 regions necessary for display of GP64 derived peptides on the BV. In one embodiment, a GP64 stem domain included amino acids 461-512; a total of 52 amino acids from the AcMNPV GP64 protein that included 22 residues from the predicted GP64 ectodomain, the 23 residues from the predicted GP64 transmembrane domain, and the 7 residue cytoplasmic tail domain. Various portions of the GP64 ectodomain were fused to the GP64 stem such that in the mature protein, the stem construct was fused to a cMyc epitope tag and either 38 (residues 21-58), 66 (residues 21-86), 138 (residues 21-158), or 274 (residues 21-294) amino acids from the N-terminus of the GP64 ectodomain. The strategy for generation of these constructs and their insertion into the baculovirus genome is illustrated in FIG. 6D. Note that dashed lines between boxes represent missing sequences.

The viruses expressing these constructs were amplified and titred in Sf9$^{Op1D}$ cells. Each virus was then used to infect Sf9 cells either alone, or by co-infection with the virus expressing a VSV G-stem protein. Each construct was thus expressed either alone or in the presence of a VSV G-stem. Infected cells (FIG. 6E) were examined for expression of the various GP64-stem containing constructs and for expression of a G-stem protein. FIG. 6E shows Western blot analysis of cell extracts from cells infected with viruses expressing the G-stem construct or the GP64-stem fusions alone (FIG. 6E, left panel) or co-infections of viruses expressing the GP64-stem fusions and a virus expressing the VSV G-stem construct (FIG. 6E, right panel). Small closed circles show the positions of the fusion proteins containing the GP64-stem, and open circles show the position of a control wild type GP64 protein containing an N-terminal cMyc epitope. An anti-cMyc monoclonal antibody was used to detect tagged proteins.

Virions from each infection were then purified and examined for the presence of the GP64-stem constructs, and for G-stem (FIG. 6F). FIG. 6F shows Western blot analysis of purified budded virions (BV) from cells infected with viruses expressing GP64-stem fusions (FIG. 6F, left panel) or co-infected with viruses expressing the GP64-stem fusions and a virus expressing the VSV G-stem construct (FIG. 6F, right panel). Most constructs were readily detected in BV alone (FIG. 6F, left panel) and the levels of GP64-stem fusions were substantially enhanced in BV that also contained G-stem (right panel; compare lanes 2, 3, and 5 between left and right panels). An anti-cMyc monoclonal antibody was used to detect tagged proteins.

The results illustrate that most constructs were expressed well in infected cells. In some cases, the G-stem construct was expressed at lower levels when the G-stem expressing virus was co-infected with the longer GP64-stem constructs (FIG. 6E, lanes 4-6). However, when purified virions were examined, G-stem protein was found in all virion preparations (FIG. 6F, right panel). In all co-infections except one, GP64-stem constructs were found in the purified virion preparations and the levels detected were in most cases substantially higher than that detected in the absence of a G-stem expressing virus (FIG. 6F, compare GP64 fusions in left and right panels). This indicates that a stem portion of GP64 can be used to target proteins to the virion, even when a G-stem construct is used to stimulate budding in the absence of wild type GP64.

There are at least two separate functions of GP64 that relate to its role in the budding and assembly of the BV. First, GP64 is required for efficient budding. The present invention determines that a very limited heterologous protein construct, a VSV-G stem, is capable of substituting for the budding function of GP64. The second functional domain of interest is the "targeting domain" that targets the GP64 protein for inclusion in the assembled virion.

To identify this BV targeting domain, a G-stem was used to provide the budding function and a series of deletion constructs were generated to map the targeting function.

Using a gp64null AcMNPV virus that expresses a G-stem from VSV, a series of GP64 constructs that contained either N- or C-terminal truncations of the ectodomain (FIGS. 6A-6C) were inserted. FIG. 6A shows a strategy for constructing a series of cMyc tagged GP64 constructs that are truncated at the N-terminus of the GP64 ectodomain. Each construct contained the GP64 signal peptide, signal cleavage site, and a cMyc epitope tag. Various amounts of the mature N-terminus of the GP64 ectodomain are deleted from the constructs. Construct names are indicated on the right of each diagram.

FIG. 6B shows Western blot analysis of cell extracts from cells infected with gp64null viruses expressing the GP64 constructs shown in FIG. 6A (FIG. 6B, left panel) or co-infected with the viruses expressing the constructs from FIG. 6A and a virus expressing the VSV G-stem construct (FIG. 6B, right panel). An anti-cMyc monoclonal antibody was used to detect tagged proteins. Small closed circles show the positions of the truncated GP64 constructs and open circles show the position of a control wild type GP64 protein containing an N-terminal cMyc epitope. Expression of each construct was detected in infected Sf9 cells. An arrowhead shows the position of the G-stem protein.

FIG. 6C shows Western blot analysis of purified budded virions from cells infected with viruses expressing the GP64 constructs shown in FIG. 6A (FIG. 6C, left panel) or co-infected with the viruses expressing the constructs from FIG. 6A and a virus expressing the VSV G-stem construct (FIG. 6C, right panel). An anti-cMyc monoclonal antibody was used to detect tagged proteins. Only the full length GP64 construct (Ntr4, 21-512) was readily detected in purified virions.

The predicted GP64 ectodomain is comprised of the predicted amino acids 21-482. Therefore, a series of gp64null viruses containing GP64 N-terminal deletions downstream of amino acid 21 (FIG. 6A) were generated. Four constructs were examined. These constructs were a control construct that contained no GP64 ectodomain deletion and three other constructs containing N-terminal deletions of 21-124, 21-270, and 21-376 amino acids, respectively. These constructs were all expressed well in infected Sf9 cells (FIG. 6B, Cell Extracts). When BV preparations (from Sf9 cells infected with each construct) were analyzed, the full length control GP64 construct was detected in abundance, indicating robust BV production and inclusion of the GP64 construct in the BV (FIG. 6C, left panel, lane 4). However, when the above N-terminally truncated GP64 constructs were examined in a similar manner, no GP64 or BV was detected (FIG. 6C, left panel, lanes 1-3). In addition, when Sf9 cells were co-infected with a) each gp64null virus expressing an N-terminally truncated GP64 construct, and b) the gp64null virus expressing the G-stem construct, only the full length GP64 construct was detected in the BV preparations (FIG. 6C, right panel, lane 4 vs. lanes 1-3, open circle). Substantial BV production was detected in each experiment that included co-infection with the gp64null virus expressing a G-stem construct, as determined by the detection of the G-stem construct in all BV preparations (FIG. 6C, right panel, arrowhead). Thus, the targeting signal appears to have been removed in all the GP64 N-terminal truncation constructs. This indicates that an important component of the targeting signal in the native GP64 protein is located within amino acids 21-125.

Use of the GP64-stem region to target proteins to the virion requires two portions of the GP64 ectodomain. When the N-terminal portion of the ectodomain was deleted, and several constructs were examined for virion production and GP64 targeting to BV (FIGS. 6A-6C), it was found that GP64 constructs that did not contain the N-terminal approximately 104 amino acids from mature GP64, were not capable of generating detectable BV (FIG. 6C, left panel) and did not target to the BV generated from G-stem mediated BV production (FIG. 6C, right panel). Thus, combined with the data from C-terminal deletion constructs (FIGS. 6D-6F), these data show that virion targeting by GP64 requires a portion of the N-terminus of the GP64 ectodomain (approximately <38 amino acids) plus the C-terminal GP64-stem described above.

FIG. 6G shows a diagrammatic representation of strategies that may be used for infection or co-infection of Sf9 cells with viruses expressing fusion proteins containing the GP64-stem and display of the GP64-stem fusions on BV. The virions on the left in this figure are originally produced in Sf9-Op1D cells as indicated. When a gp64null virus that expresses either the GP64-stem or a GP64-stem fusion is used to infect Sf9 cells, virion budding is partially restored. Infection of Sf9 cells with a gp64null virus and expression of VSV G-stem results in full restoration of budding. In fact, the budding is robust and results in budded virions containing VSV G stem. Co-infection with a gp64null virus expressing VSV G-stem and a gp64null virus expressing a GP64-stem fusion optimizes virion budding and display such that virion budding is robust and GP64-stem fusions are displayed on the budded virion envelope.

Thus, in yet another embodiment of the present invention, a heterologous gene or peptide is inserted into a construct, between a small portion of the N-terminus of GP64 (for example, approximately 38 amino acids of the ectodomain), and a GP64-stem (the GP64 ecto-TM-CTD construct). As an example, this construct may include: 58 amino acids from the N-terminus of GP64 (the signal peptide and 38 amino acids of the ectodomain), the heterologous protein or peptide, a small portion of the C-terminus of the GP64 ectodomain (such as the 22 amino acids included in the GP64 stem constructs described in the studies included here) plus the GP64 TM and CTD. The N-terminal 58 amino acids of GP64 combined with a GP64-stem could thereby rescue budding in the gp64null baculovirus.

Using small heterologous proteins or peptides in another embodiment may be particularly useful for surface display with higher budding efficiency, using only the above GP64-derived construction and in the absence of wild type GP64 or a G-stem.

Targeting of proteins or peptides to budded baculovirus virions could also be accomplished by fusing the heterologous peptide or protein for display, onto a stem region derived from a baculovirus F protein, such as Ac23, SeF, or LdF. A suitable protein would comprise a) an N-terminal signal peptide and the signal peptide cleavage site derived from either the heterologous protein, a baculovirus protein such as GP64, or from a baculovirus F protein, b) all or a portion of the ectodomain of the heterologous peptide or protein for display, c) a moderate or small portion of the F protein ectodomain, and d) the transmembrane domain and cytoplasmic tail domains of the F protein. Because F proteins such as Op21, Ac23, SeF, and LdF have been shown to be present in the budded virions of OpMNPV, AcMNPV, SeMNPV, and LdMNPV, respectively, portions of these F proteins or others may be used to target heterologous proteins to the virion.

FIG. 7 shows strategies for display of heterologous proteins on the surface of gp64null AcMNPV budded virions, as either native proteins, as fusion proteins with the VSV G-stem, or as fusion proteins with a portion of the GP64 protein (GP64-stem). This figure shows that baculovirus genomes with a deleted gp64 gene can be propagated as infectious viruses, using the cell line Sf9-OP1D, which expresses the OpMNPV GP64 protein. As discussed above with respect to FIG. 2, a baculovirus genome contains a deleted gp64 gene (gp64 knockout, $vAc^{64-}$) and those viruses can be propagated in the cell line expressing OpMNPV GP64. When the GP64 null virus infects Sf9-Op1D, the virus without the gp64 gene can bud and propagate, thus resulting in budding of a GP64null virus with OpMNPV GP64 protein derived from the cell line. A gene encoding the "stem" region of the VSV G protein may be inserted into the gp64 knockout (vAc/G-Stem) and that virus propagated in the cell line expressing OpMNPV GP64. When the GP64null/G-stem+ virus infects Sf9 cells, virion budding is restored, resulting in budded virions with VSV G stem.

In another embodiment, both the gene encoding the "stem" region of the VSV G protein and a gene encoding an envelope or membrane protein are inserted into the gp64 knockout. When these virions infect Sf9 cells, VSV G stem mediates efficient budding and the resulting virions carry both VSV-G stem and the new membrane or envelope protein. In yet another embodiment, both the gene encoding the "stem" region of the VSV G protein and a chimeric G-stem fusion are inserted into the gp64 knockout. When infected into Sf9 cells, the VSV G stem mediates efficient budding and the chimeric G-stem fusion is targeted to the virion membrane. In still another embodiment, both the gene encoding the VSV G stem and genes encoding a chimeric GP64 fusion protein are inserted into the gp64 knockout. When used to infect Sf9 cells, VSV G stem mediates efficient budding and the chimeric GP64 fusion is targeted to the virion membrane.

Figure 8:
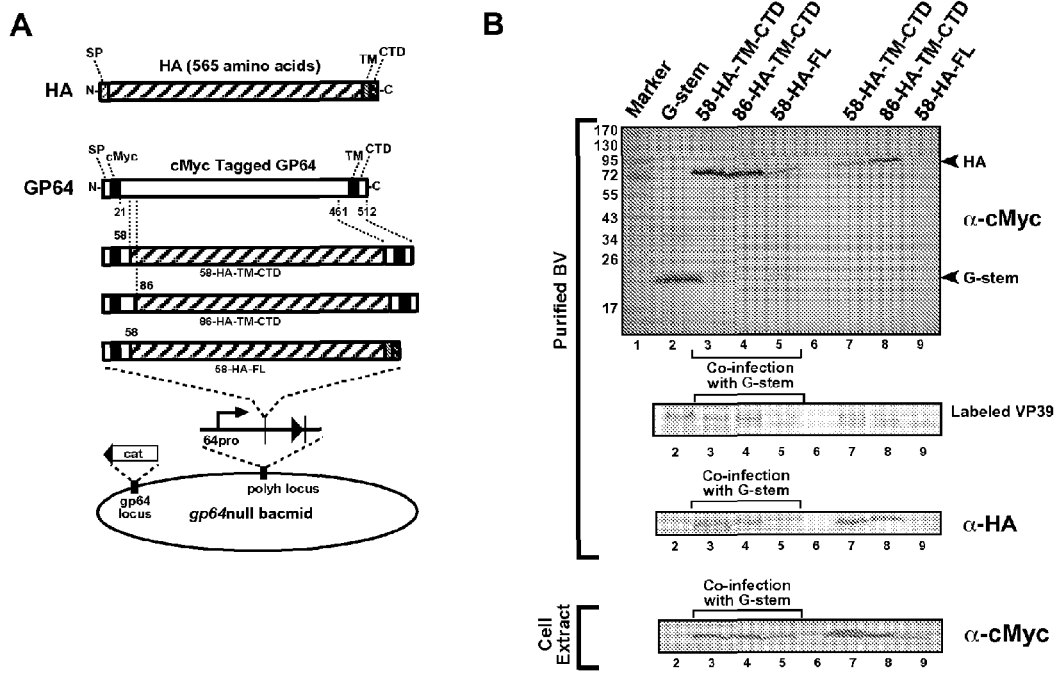
FIG. 8A shows a strategy for generating HA-GP64 fusions and insertion of chimeric HA constructs into the polyhedrin locus of a gp64null AcMNPV bacmid.
FIG. 8B shows Western blot analysis of BV preparations from viruses expressing HA-GP64 fusions and co-infection with a G-stem expressing virus.

Recombinant baculoviruses expressing chimeric HA proteins were constructed as an example of baculovirus virion display of heterologous proteins. FIGS. 8A and 8B show enhanced targeting of HA fusions to AcMNPV BV and enhanced budding mediated by the G-stem construct. Chimeric HA-GP64 protein constructs were generated by fusing the HA ectodomain (18-528) with the GP64 signal peptide and various portions from the N terminus of the GP64 ectodomain, and the GP64-stem region or the native HA TM and CTD domains. Constructs were expressed under the control of the gp64 promoter. Two chimeric HA-GP64 proteins each contained an N-terminal cMyc epitope tag and either 38 or 66 residues of the GP64 ectodomain (at the N terminus), and a 91 amino acid GP64-stem sequence at the C terminus (constructs 58-HA-TM-CTD and 86-HA-TM-CTD). Construct 58-HA-FL contains a cMyc epitope tag, 38 amino acids from the N terminus of the GP64 ectodomain, and the HA ectodomain, TM, and CTD (residues 18-565).

FIG. 8B shows Western blot analysis of BV preparations. Purified BV preparations derived from cells infected with viruses expressing HA fusion proteins (lanes 7, 8 and 9) or co-infected with viruses expressing HA fusion proteins and a virus expressing the VSV G-stem construct (lanes 3, 4 and 5)

were examined for the presence of envelope protein constructs using an anti-cMyc antibody (Purified BV, top panel) or an anti-HA antibody (Purified BV, α-HA, lower panel). VP39 from purified $^{35}$S-Methionine labeled progeny BV (Purified BV, middle panel, Labeled VP39) was detected by PhosphorImager™ analysis and used to more directly compare levels of progeny BV production. A control infection with only the virus expressing the cMyc-tagged G-stem construct is shown in lane 2. Cell extracts from the above preparations were also examined for protein expression using anti-cMyc antibody.

The influenza A/WSN/33 HA gene encoding the ectodomain (amino acids 18 to 528) was PCR amplified from plasmid pEWSN-HA (Neumann et al., 2000, Journal of Virology 74:547-551, incorporated herein by reference). A forward primer (Kpn-HA Forward) with a Kpn1 restriction site engineered into the 5' end (SEQ ID NO: 1, see Sequence Listing; which included sequence immediately downstream of the HA signal peptide), was used in combination with a downstream primer. The downstream primer (SEQ ID NO: 2) contained a KpnI site engineered for in-frame insertion of the HA gene into vector pFB-gp64sig-cmyc-58-TM-CTD or pFB-gp64sig-cmyc-86-TM-CTD, which are pFastBac-derived plasmids containing the gp64 promoter, and sequence encoding the gp64 signal peptide and cleavage site, a cMyc tag, 38 or 66 amino acids of the GP64 N-terminal ectodomain and a KpnI cloning site, followed by 21 amino acids from the GP64 C-terminal ectodomain and the GP64 TM and GP64 CTD. The PCR product was digested with Kpn1 and ligated into the Kpn1 sites of vector pFB-gp64sig-cmyc-58-TM-CTD or pFB-gp64sig-cmyc-86-TM-CTD, to generate constructs containing the HA ectodomain and the GP64-stem. The resulting constructs were designated pFB-58-HA-TM-CTD and pFB-86-HA-TM-CTD, respectively. Thus, each construct expresses a protein that contains an N-terminal cMyc tag, a variable portion of the mature N-terminal region of the GP64 protein, the HA ectodomain and the GP64-stem region (see FIG. 8A). In addition, a construct containing the GP64 promoter and signal peptide combined with the HA ectodomain, HA TM and CTD (HA amino acids 18 to 565) was also generated by first PCR amplifying the downstream portion of the HA gene from plasmid pEWSN-HA (25) and inserting it into a pFastbac plasmid. The HA sequences were amplified using the same forward primer (Kpn-HA Forward) in combination with a downstream primer (SEQ ID NO: 3). The downstream primer contained an HindIII site engineered for insertion of the HA gene into vector pFB-gp64sig-cmyc-58-TM-CTD. The resulting plasmid pFB-58-HA-FL encodes a protein that contains an N-terminal cMyc tag, a portion of the mature N-terminal region of the GP64 protein, the HA ectodomain and the HA TM and CTD region (FIG. 8A, 58-HA-FL).

G-stem and GP64 domains necessary for budding and virion targeting may be effectively used together. Portions of the GP64 protein alone were examined to determine if they may be used to target foreign proteins to gp64null virions. The ectodomain of influenza HA (A/WSN/33) was fused between the C-terminal GP64-stem and various portions of the N-terminal ectodomain to determine if the mapped targeting and budding domains of GP64 were sufficient for rescue of budding and targeting of a heterologous protein to the virion (FIG. 8A). N-terminal fusions contained the GP64 signal peptide, a cMyc epitope, and 38 or 66 amino acids from the N terminus of the GP64 ectodomain. The C terminus of each construct was comprised of either the 52 amino acid GP64 stem region (58-HA-TM-CTD; 86-HA-TM-CTD) or the wild type HA TM and CTD (FIG. 8A, 58-HA-FL). Each construct was inserted into a gp64null AcMNPV genome and the resulting viruses were propagated in Sf9$^{Op1D}$ cells. Sf9 cells were then infected with each virus either alone, or in combination with a virus expressing the G-stem construct. On Western blots of purified BV preparations challenged with an anti-cMyc antibody, the HA ectodomain fusions were detected abundantly (FIG. 8B, upper panel, HA). The identity of HA fusions was also confirmed by Western blot analysis with an anti-HA polyclonal antiserum (FIG. 8B, Anti-HA). Co-infection of each of the HA-fusion constructs with a virus expressing the G-stem construct resulted in higher levels of detection of the HA-fusions, and in these constructs the G-stem was detected at lower levels. When expressed in the presence of the G-stem construct, two of the ectodomain fusions (58-HA-TM-CTD and 86-HA-TM-CTD) were detected at levels that appeared to be similar to the abundant expression of the G-stem construct alone. Although the HA construct that contained its own TM and CTD domains was expressed and detected on the purified BV, the levels were clearly lower than that of either construct containing the GP64 stem region (FIG. 8B, lane 5 versus lanes 3 and 4; lane 9 versus lanes 7 and 8). Relative differences in budded virion production were more directly observed by examining the relative levels of the major capsid protein (VP39) in purified labeled budded virion preparations (FIG. 8B, Labeled VP39, compare lane 5 versus lanes 3 and 4; lane 9 versus lanes 7 and 8). Thus, the combined use of G-stem stimulated budding and the GP64 targeting domain resulted in more efficient display of this heterologous protein on the AcMNPV BV. Most prior studies of virion display have utilized protein expression from the very strong polyhedrin or p10 promoter whereas the constructs generated in the present invention were generated with the native GP64 early/late promoter. Higher expression levels may lead to a higher abundance of the displayed protein on the cell surface after optimizing the budding and targeting as described herein.

By generating viruses that express chimeric influenza virus hemagllutinin (HA) proteins containing the GP64 targeting domain and coinfecting those viruses with a virus expressing the G-stem construct, the present invention shows enhanced display of the HA protein on gp64null AcMNPV budded virions. The combined use of gp64null virions, VSV G-stem enhanced budding, and GP64 domains for targeting heterologous proteins to virions is useful for applications including, but not limited to, targeted transduction of mammalian cells and vaccine production.

Specific examples of methods used to practice the above-described embodiments of the invention are detailed below. Other methods, known by those skilled in the art, could alternatively be used without deviating from the spirit of the invention.

Construction of the gp64-Null AcMNPV Bacmid

The gp64 gene of an AcMNPV bacmid (bMON14272; Invitrogen) was deleted from the AcMNPV genome by a modification of the method taught in Bideshi and Federici, J Gen Virol 81:1593-1599, 2000, herein incorporated by reference, as reported in Lung et al. Briefly, a chloramphenicol resistance gene (cat) cassette was amplified by PCR and cloned to generate plasmid pCh1R-CRIIblunt. The insert containing the cat cassette was excised from pCh1R-CRIIblunt and was used to replace the SpeI-BglII fragment (containing the gp64 gene) in pAcEcoHΔSma, a plasmid containing the AcMNPV gp64 ORF and flanking sequences (13), resulting in generation of plasmid, pAcEcoHΔSma, gp64 (Ch1R). An EcoRI and HindIII fragment was excised and gel purified, then cotransformed with AcMNPV bacmid bMON14272. A colony resistant to kanamycin and chloramphenicol was selected and analyzed and named vAc$^{gp64-}$. The virus vAc$^{gp64-}$ was propagated in Sf9$^{Op1D}$ cells which constitutively express the OpMNPV GP64 protein.

Donor Plasmids Containing G-Stem Fusion Protein Genes

To express a VSV G-Stem construct in the context of a gp64null AcMNPV virus, a donor plasmid construct designated pFBcMyc-G-Stem was generated. A truncated version of the vesicular stomatitis virus (VSV) G protein, containing 91 amino acides that included 42 amino acids of C-terminal ectodomain, plus the transmembrane (TM) and cytoplasmic terminal domains (CTD) (20 amino acids and 29 amino acids, respectively), was generated by PCR-mediated mutagenesis in the following manner. A forward primer with an EcoR1 restriction site engineered into the 5' end (SEQ ID NO: 4), was used in combination with a reverse primer that contained an XbaI site (SEQ ID NO: 5) to amplify the "stem" portion of the VSV G gene from a wild type VSV G DNA template (pSM8141-VSV G) (11). Thus, EcoRI and XbaI restriction sites were engineered into the 5' and 3' ends, respectively, of the G-Stem PCR product. The PCR product was digested with EcoRI and XbaI, purified, and ligated into the EcoRI and XbaI sites of vector pdFB-gp64sig-cMyc, a pFastBac-derived plasmid containing the gp64 promoter, the signal peptide and cleavage site, followed by a cMyc epitope tag and a cloning site (FIG. 1B). The resulting construct was named pFBcMyc-G-stem. Thus, the truncated form of the VSV G gene that was cloned into vector pdFB-gp64sig-cMyc expresses a protein that contains an N-terminal cMyc epitope tag linked by a Phe residue to the truncated VSV G protein.

Transpositions of inserts from donor plasmids into the gp64-null bacmid were initially detected by gentamicin resistance and blue-white screening according to the BAC-to-BAC manual (Invitrogen), and further confirmed by PCR analysis and by DNA sequencing. Cells stably expressing OpMNPV GP64 (cell line Sf9$^{Op1D}$) were transfected with each bacmid DNA and the resulting viruses were harvested from cell supernatants and titred on Sf9$^{Op1D}$ cells. The resulting virus was designated vAc/G-Stem.

A series of plasmids was also constructed in which C-terminal truncations of GP64 or the enhanced green fluorescent protein (EGFP) coding region were cloned in frame between the cMyc epitope and the VSV G Stem domains (FIGS. 1B, 5A and 5B) of plasmid pFBcMyc-G-Stem. DNA fragments encoding C-terminally truncated portions of the GP64 open reading frame were PCR amplified from a wild type (wt) AcMNPV DNA template. A single forward primer with an EcoRI restriction site engineered into the 5' end (SEQ ID NO: 6; corresponding to a sequence 57 base pairs downstream of the gp64 start codon), was used in combination with a downstream primer specific for each truncation (Table 1). Each downstream primer contained an EcoRI site engineered for in-frame insertion of the AcMNPV gp64 gene into vector pFBcMyc-G-Stem. Thus, EcoRI restriction sites were engineered into both 5' and 3' ends, of each PCR product. Each PCR product was digested with EcoRI, purified, and ligated into the EcoRI sites of vector pFBcMyc-G-Stem, to generate a truncated GP64 ORF fused in-frame at the N-terminus of the VSV G-Stem. Each construct was confirmed by PCR to confirm the correct orientation of the insertions and also by sequencing across the junctions. The resulting viruses were produced as described above and the viruses were designated: vAc/130-G-Stem, vAc/152-G-Stem, vAc/160-G-Stem, vAc/166-G-Stem, vAc/175-G-Stem and vAc/EGFP-G-Stem.

Constructs encoding N-terminal truncations of the GP64 ectodomain (see FIG. 6A) express proteins containing an N-terminal c-Myc epitope tag linked by a Phe residue to a portion of the GP64 ectodomain truncated at the N terminus of the mature GP64 protein.

Analysis of Progeny Virion Production by $^{35}$S-Methionine Labeling

Progeny virions from infections with viruses vAc$^{gp64-/Acgp64}$, vAc$^{gp64-}$ or vAc/G-Stem were labeled with $^{35}$S-methionine in the following manner. Sf9 cells ($1\times10^7$ cells) were plated in a T-25 flask (Corning Inc.). After cells were allowed to attach for 1 hour, they were infected with recombinant virues at an MOI of 10 for 1 hour. At 29 hours post infection, the cells were starved by incubation in 3 ml methionine-free Grace's medium (Invitrogen) for 1 hour, followed by addition of $^{35}$S-EasyTag Express protein labeling mix (1175.0 Ci/mmol, Perkin-Elmer) to a final concentration of 10 µCi/ml. At 37 hours post infection, unlabeled methionine was added to a final concentration of 10 mM and cells were incubated at 27° C. for an additional 48 hours. Supernatants were harvested and virions purified by pelleting through a 25% sucrose cushion at 100,000×g for 90 minutes at 4° C. in a Beckman SW60 rotor. Virus pellets were resuspended in 300 µl Phosphate Buffered Saline (PBS, pH 6.2).

Construction of Plasmids and Baculoviruses Encoding Constructs Containing a GP64-Stem Region A series of plasmids encoding the C-terminal GP64 region (the GP64-stem region) and varying portions of the GP64 ectodomain, was generated by the following strategy: First, DNA fragments containing variable portions of the GP64 open reading frame were PCR amplified from a wild type (wt) AcMNPV DNA template. A forward primer with an EcoR1 restriction site engineered into the 5' end (SEQ ID NO: 6; which included sequence immediately downstream of the gp64 signal peptide), was used in combination with a downstream primer specific for each truncation (Table 1).

TABLE 1

PCR primers for amplification of EGFP and portions of GP64

| Forward Primer: |
| --- |
| SEQ ID NO: 6 |
| Reverse Primers: |
| 130 reverse: SEQ ID NO: 7 |
| 152 reverse: SEQ ID NO: 8 |
| 160 reverse: SEQ ID NO: 9 |
| 166 reverse: SEQ ID NO: 10 |
| 175 reverse: SEQ ID NO: 11 |
| EGFP Primers: |
| EGFP forward: SEQ ID NO: 12 |
| EGFP reverse: SEQ ID NO: 13 |

TABLE 2

PCR primers for amplification of portions of GP64

| Forward Primer: |
| --- |
| SEQ ID NO: 6 |
| Reverse Primers: |
| Tyr58: SEQ ID NO: 14 |
| Arg86: SEQ ID NO: 15 |
| Val158: SEQ ID NO: 16 |
| Gly294: SEQ ID NO: 17 |

Each downstream primer contained a KpnI site engineered for in-frame insertion of the AcMNPV gp64 gene into vector pFB-gp64sig-cmyc-TM-CTD, a pFastBac-derived plasmid containing the gp64 promoter, and sequence encoding the signal peptide and cleavage site, a cMyc tag and a cloning site, followed by 21 amino acids of GP64 C-terminal ectodomain, plus the GP64 transmembrane (TM) and GP64 cytoplasmic tail domains (CTD). Each PCR product was digested with EcoRI and Kpn1 and ligated into the EcoRI and Kpn1 sites of vector pFB-gp64sig-cmyc-TM-CTD, to generate a series of constructs each containing the GP64-stem and varying portions of the GP64 ectodomain (FIG. 6). Thus, each construct expresses a protein that contains an N-terminal cMyc tag, a portion of the mature N-terminal region of the GP64 protein, and the GP64-stem region. Each construct was confirmed by sequencing across the junctions. The resulting viruses were produced as described above and the viruses were designated: vAc/58-TM-CTD, vAc/86-TM-CTD, vAc/158-TM-CTD and vAc/294-TM-CTD (FIG. 6B).

Co-Infections

For co-infection experiments, Sf9 cells (1×10$^5$ cells) seeded on each well of a E-well-plate were co-infected at a total MOI of 10 with the equal infectious units of the vAc/G-Stem virus plus one of the following viruses: vAc/58-TM-CTD, vAc/86-TM-CTD, vAc/158-TM-CTD or vAc/294-TM-CTD. Progeny virions derived from co-infection experiments were purified and analyzed as described above. Viruses used for coinfections included the gp64null baculovirus, a control virus and those illustrated in FIGS. 6A, 6D and 8A.

Western Blot Analyses

Cell lysates were prepared by washing cultured cells with phosphate buffered saline (PBS) and resuspending cells in NET buffer (20 mM Tris, pH 7.5, 150 mM NaCl, 0.5% deoxycholate, 1.0% Nonidet P-40, 1 mM EDTA) to which a protease inhibitor cocktail (Complete; Roche Applied Science) was added according to the manufacturer's instructions. NET buffer (500 μl) was added to 1×10$^6$ cells and incubated for 30 minutes at 4° C., and then nuclei were removed by pelleting at 4° C. for 10 minutes at 18,000×g. Virus purification was performed as described above. For Western blot analysis, 10 μl of the cell lysate or purified viruses were mixed with 10 μl of 2× Laemmli buffer (125 mM Tris, 2% sodium dodecyl sulfate (SDS), 5% 2-mercaptoethanol, 10% glycerol, 0.001% bromophenol blue, pH 6.8) and heated to 100° C. for 5 minutes prior to SDS-10% polyacrylamide gel electrophoresis (SDS-PAGE). Gels were blotted onto Immobilon-P membranes (Millipore) and blocked overnight at 4° C. in TBST (25 mM Tris, pH 7.6, 150 mM NaCl, 0.1% Tween 20, 5% powdered milk). Blots were incubated for 1 hour at room temperature with the following primary antibodies diluted in TBST: anti cMyc MAb (from hybridoma supernatant) diluted 1:1000, anti-VP39 MAb diluted 1:1000, anti-HA (chicken polyclonal antisera) diluted 1:100, or anti-VSV G (MAb P5D4) diluted 1:10,000. After washing 3 times in TBST, blots were incubated with a secondary antibody consisting of a goat anti-mouse IgG-alkaline phosphatase conjugate (Promega) at a dilution of 1:10,000. Western blots were processed as described in Blissard et al., 1992, J. Virol. 66:6829-6835, herein incorporated by reference.

Fluorescence Microscopy

Sf9 cells (1×10$^5$ cells) seeded on 6-well-plate were infected at an MOI of 10 with the vAc/EGFP-G-Stem virus expressing EGFP-G-Stem and incubated for 24 and 48 hours. Epiflorescence microscopy was performed with an inverted IX70 microscope (Olympus).

It will be apparent that permutations of the methods and strategies outlined above may be useful to rescue budding from GP64-protein-null baculoviruses. It will also be apparent that permutations of the disclosed G-stem compositions and constructs thereof are possible. Using methods disclosed herein one may perform experiments to determine precise quantitative differences in virion budding when constructs containing different VSV G protein fragments are expressed in a baculovirus (or otherwise provided) and thereby identify alternate G-stem compositions and constructs suitable for the invention. The use of G-stem or GP64-stem constructs as chimeric fusions with heterologous proteins to target proteins to the virion membrane or envelope could be used separately or in combination with any of the enhanced budding embodiments disclosed herein. Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. A method of restoring efficient budding capability in a gp64null baculovirus where the baculovirus envelope glycoprotein gp64 is absent in the baculovirus, comprising the step of a) inserting a Vesicular Stomatitis Virus G-stem construct encoding amino acids 421 to 511 of a Vesicular Stomatitis Virus G-stem protein into the viral genome of the baculovirus, thereby restoring efficient budding capability in the baculovirus.

2. The method of claim 1, further comprising, prior to step a), the step of b) knocking out the gene encoding the baculovirus envelope glycoprotein gp64 in the baculovirus.

3. The method of claim 1, wherein the gp64null baculovirus is derived from wild type *Autographa californica* multicapsid nucleopolyhedrovirus or a gp64+ *Autographa californica* multicapsid nucleopolyhedrovirus bacmid.

4. The method of claim 3, further comprising, prior to step a), the step of b) knocking out a gp64 gene in the *Autographa californica* multicapsid nucleopolyhedrovirus bacmid.

5. The method of claim 1, further comprising the step of producing baculovirus virions.

* * * * *